(12) United States Patent
Gonopolskiy et al.

(10) Patent No.: US 9,931,078 B2
(45) Date of Patent: Apr. 3, 2018

(54) NEAR-INFRARED SPECTROSCOPY SENSOR WITH LIGHT SHEET

(75) Inventors: Oleg Gonopolskiy, West Bloomfield, MI (US); Arik Anderson, Birmingham, MI (US)

(73) Assignee: COVIDIEN LP, Mansfield, MA (US)

( * ) Notice: Subject to any disclaimer, the term of this patent is extended or adjusted under 35 U.S.C. 154(b) by 1251 days.

(21) Appl. No.: 12/832,346

(22) Filed: Jul. 8, 2010

(65) Prior Publication Data

US 2011/0009721 A1   Jan. 13, 2011

Related U.S. Application Data

(60) Provisional application No. 61/224,005, filed on Jul. 8, 2009.

(51) Int. Cl.
*A61B 5/00* (2006.01)
*A61B 5/1455* (2006.01)

(52) U.S. Cl.
CPC ........ *A61B 5/6833* (2013.01); *A61B 5/14552* (2013.01); *A61B 5/6826* (2013.01); *A61B 5/6838* (2013.01)

(58) Field of Classification Search
CPC ............................ A61B 5/0059; A61B 5/0075
USPC ........................................................ 600/323
See application file for complete search history.

(56) References Cited

U.S. PATENT DOCUMENTS

| 4,830,014 | A | 5/1989 | Goodman et al. |
|---|---|---|---|
| 5,388,357 | A * | 2/1995 | Malita .............................. 40/570 |
| 6,745,061 | B1 * | 6/2004 | Hicks et al. ................... 600/344 |
| 7,052,924 | B2 | 5/2006 | Daniels et al. |
| 7,161,590 | B2 | 1/2007 | Daniels |
| 2008/0076982 | A1 | 3/2008 | Ollerdessen et al. |
| 2008/0080163 | A1 * | 4/2008 | Grote, III et al. .............. 362/23 |
| 2009/0163775 | A1 | 6/2009 | Barrett et al. |
| 2009/0323067 | A1 * | 12/2009 | Medina ......................... 356/432 |

OTHER PUBLICATIONS

International Search Report for PCT/US2010/041372 dated Oct. 27, 2010.

* cited by examiner

*Primary Examiner* — Hien Nguyen

(57) ABSTRACT

A sensor includes a sensor pad configured to be disposed on a portion of a patient's body. A light sheet is disposed on the sensor pad and has a first substrate and a second substrate spaced from one another. The light sheet further includes a light source configured to emit near-infrared light and a light detector configured to detect near-infrared light. The light source and the light detector are disposed between the substrates. The sensor pad is configured to allow light generated by the light source to travel through the portion of the patient's body to the light detector. The light received by the light detector is indicative of oxygen saturation of the portion of the patient's body through which the light travelled.

15 Claims, 6 Drawing Sheets

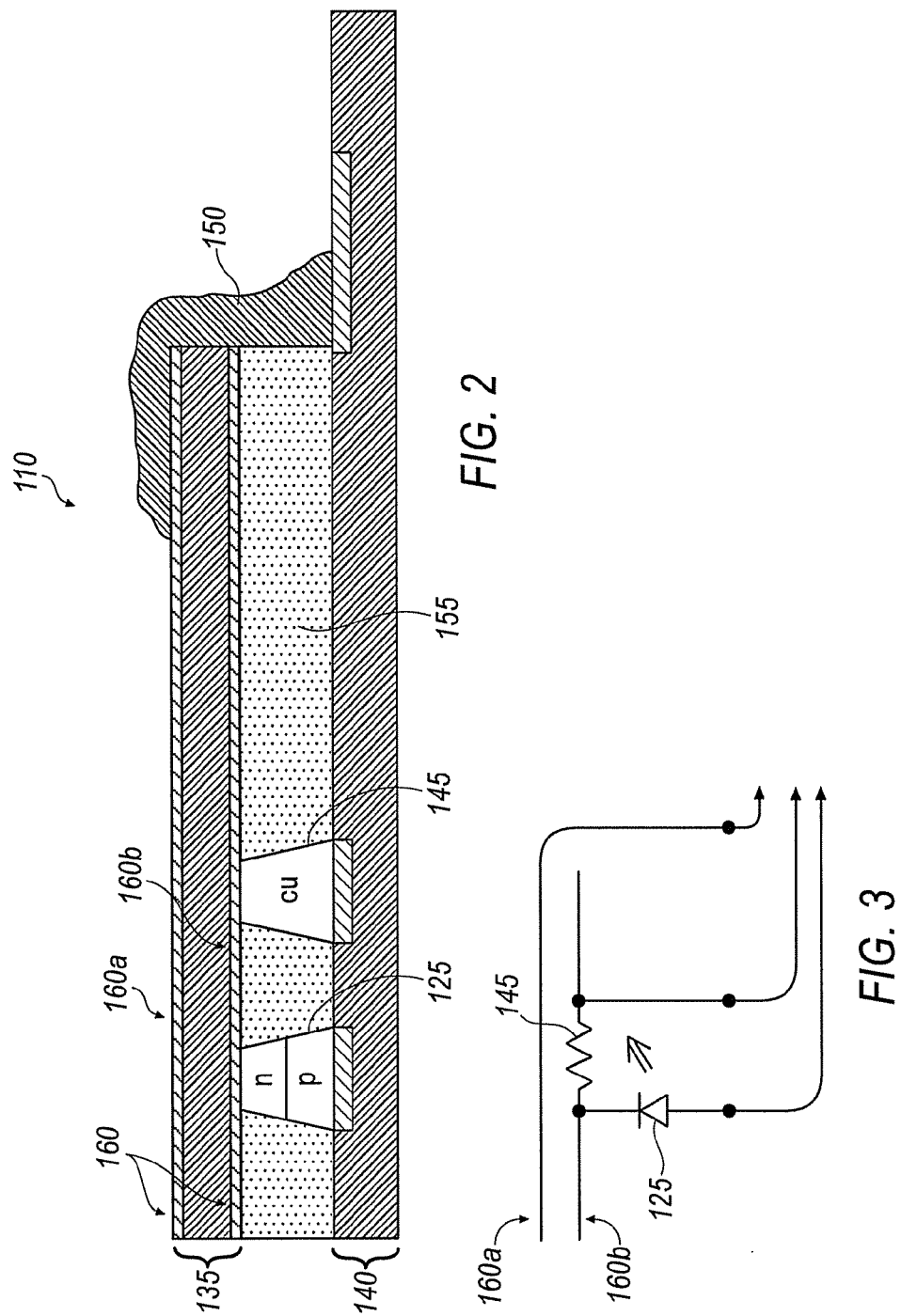

NEAR-INFRARED SPECTROSCOPY SENSOR WITH LIGHT SHEET

CROSS-REFERENCE TO RELATED APPLICATIONS

This application claims priority to U.S. Ser. No. 61/224,005 filed on Jul. 8, 2009, the contents of which are incorporated herein by reference.

BACKGROUND

Near-Infrared spectroscopy is a non-invasive medical technique used to measure the oxygen saturation of a patient's blood or tissue. When oxygen saturation in patients drops below a certain threshold (e.g., during an ischemic event), the patient experiences hypoxemia or ischemia. Some patients are at a higher risk for low oxygen saturation than others. For instance, physicians may monitor the oxygen saturation of blood and tissue in a prematurely-born neonate to ensure that the neonate's blood and tissue receives adequate amounts of oxygen. The physician may take action if the patient's oxygen saturation levels prove to be too low.

Measuring oxygen saturation presents challenges. For example, existing oxygen sensors are sometimes too rigid to properly fit onto the patient's body, making it difficult to accurately measure oxygen saturation. Accordingly, an oxygen sensor that is flexible enough to fit the contours of the patient's body is needed.

BRIEF DESCRIPTION OF THE DRAWINGS

FIG. 2 illustrates an exemplary cross-sectional view of a sensor with the light active sheet.

FIG. 3 illustrates an exemplary representative circuit of the sensor of FIG. 2.

DETAILED DESCRIPTION

A physiological sensor includes a sensor pad configured to be disposed on a portion of a patient's body. A light sheet is disposed on the sensor pad and has a first substrate and a second substrate. A light source configured to emit near-infrared light and a light detector configured to detect near-infrared light are disposed between the substrates. The sensor pad is configured to allow light generated by the light source to travel through the portion of the patient's body to the light detector. The light received by the light detector is indicative of oxygen saturation of the portion of the patient's body through which the light travelled. A physiological sensor that includes a light sheet with a light source and light detector as described herein provides the flexibility necessary to allow the sensor to fit the contours of a patient's body, including a neonate's body.

Figure 1:
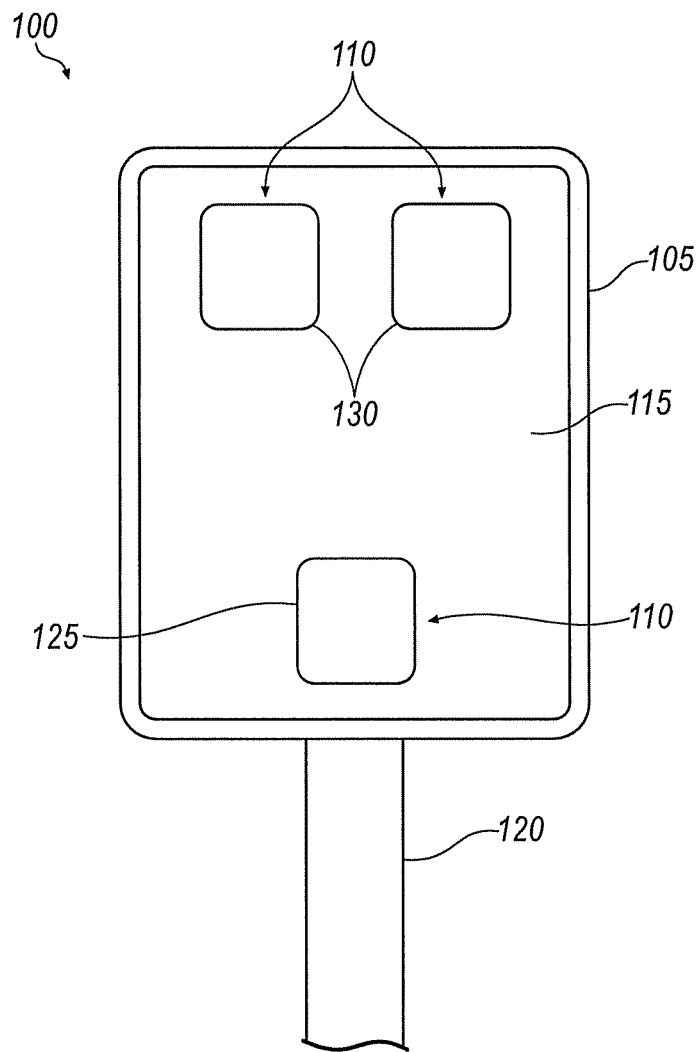
FIG. 1 illustrates an exemplary sensor having a light active sheet.

FIG. 1 illustrates a cross-sectional view of an exemplary sensor 100 having a light active sheet 105. The sensor 100 may take many different forms and include multiple and/or alternate components and facilities. While an exemplary sensor 100 is shown in FIG. 1, the exemplary components illustrated in the figures are not intended to be limiting. Indeed, additional or alternative components and/or implementations may be used.

As illustrated in FIG. 1, the sensor 100 includes a sensor pad 105, a light sheet 110 disposed on the sensor pad 105, a light blocking pattern 115, and a cable 120 for connecting the sensor 100 to a controller (not shown in FIG. 1) and display device (not shown).

The sensor pad 105 may include any material that allows the sensor 100 to be placed on a portion of a patient's body. The sensor pad 105 may include an adhesive, such as a pressure sensitive adhesive, on one surface that holds the sensor 100 in a fixed location relative to the patient's body. The sensor pad 105 may be opaque to prevent ambient light from interfering with the sensor 100. Moreover, the sensor pad 105 may be formed from a non-conductive material.

The light sheet 110 is disposed on the sensor pad 105, and in one exemplary implementation, the light sheet 110 is at least partially surrounded by the sensor pad 105. The light sheet 110 is configured to act as a light source 125 and a light detector 130. For instance, the light sheet 110 is configured to generate light in the near-infrared region of the electromagnetic spectrum. The light generated by the light sheet 110 may travel through a portion of the patient's body over which the sensor 100 is located. The light sheet 110 may also be used to receive the light after it has travelled through the patient's body. The light received by the light sheet 110 after travelling through the patient's body is indicative of the oxygen saturation of the tissue through which the light travelled. The sensor 100 may include any number of light sheets 110. For instance, the sensor 100 may include a single light sheet 110 that both generates and receives near-infrared light. Alternatively, the sensor 100 may include multiple light sheets 110 where, for instance, one or more light sheets 110 generate near-infrared light while one or more other light sheets 110 receive the near-infrared light.

The light blocking pattern 115 may include any material that may be disposed on the light sheet 110 that separates the light sheet 110 into separate sections. For instance, one section of the light sheet 110 may be used to generate near-infrared light while another section may be used to receive near-infrared light. The light blocking pattern 115 may include, for instance, carbon ink. Alternatively, in one exemplary approach, the light blocking pattern 115 may be integrally formed with the sensor pad 105.

The cable 120 is used to connect the sensor 100 to a controller and/or display device. The cable 120 may include one or more wires that can carry control signals to the light sheet 110 to illuminate the light sheet 110. Moreover, the cable 120 may include one or more wires that can transmit signals indicating the luminosity of the light detected by the light sheet 110 to the controller and or display device. The controller may determine oxygen saturation based on the luminosity or other characteristic of the light detected by the light sheet 110 and transmitted via the cable 120.

FIG. 2 illustrates an exemplary cross-sectional view of the light sheet 110 configured to generate near-infrared light. The light sheet 110 includes a first substrate 135 and a second substrate 140 spaced from one another, a light source 125, a resistive element 145, a conductive adhesive 150, and a non-conductive adhesive 155.

The first substrate 135 is substantially transparent to near-infrared light and includes two layers 160 of an electrically conductive pattern with a non-conductive spacer material, such as Mylar® insulating material disposed therebetween. As used herein, substantially transparent may include any material that provides a flat wavelength response for light within the near-infrared spectrum. Thus, the material may absorb light outside the near-infrared spectrum and may even absorb a small amount of light within the near-infrared spectrum (e.g., the absorption spectrum of the material will have small or no peaks within a majority or all of the near-infrared spectrum). The two electrically conductive pattern layers 160 (e.g., a top layer 160A and a bottom layer 160B) may be formed from a conductive transparent material such as iridium titanium oxide. The conductive pattern layers 160 may be formed from any other material that is substantially transparent at least to near-infrared light. The top layer 160A may act as an electrical shield. The top layer 160A may further include an adhesive to adhere the sensor 100 to the patient's skin. The first substrate 135 is substantially transparent at least to near-infrared light so that light generated by the light sheet 110 may be transmitted to the patient.

The second substrate 140 may be formed from a flexible material and include a flexible printed circuit board, which helps the sensor 100 conform to a shape of a portion of the patient's body. The second substrate 140 may include a plurality of printed traces 165 in electrical communication with the cable 120 to allow control signals to reach various components in the light sheet 110. In one exemplary approach, the second substrate 140 is opaque to prevent ambient light from interfering with the sensor 100.

The light source 125 may include any device, such as a semiconductor, that is configured to emit near-infrared light when provided with a control signal. The light source 125 may include a P-N junction semiconductor having an anode on the P side and a cathode on the N side. The anode of the light source 125 is electrically connected to the traces on the second substrate 140 while the cathode of the light source 125 is electrically connected to the bottom layer 160B of the first substrate 135. As electricity flows from the P side to the N side, near-infrared light is generated. Of course, other wavelengths of light may alternatively be generated. The light sheet 110 may include any number of light sources 125.

The resistive element 145 may be used to control the current through the light source 125. In one exemplary approach, the resistive element 145 has a relatively low resistance. Indeed, the resistive element 145 may be formed from a conductive material, such as copper.

The conductive adhesive 150 may be used to electrically connect the first and second substrates 135, 140, for instance, so that the conductive portions of the first and second substrates 135, 140 are at the same potential. In one exemplary approach, the conductive adhesive 150 may electrically connect the layers 160 of the conductive pattern of the first substrate 135 to one or more of the traces of the second substrate 140. The conductive adhesive 150 may be formed from any conductive adhesive material such as a silver epoxy.

The non-conductive adhesive 155 is disposed between the first substrate 135 and the second substrate 140. The light source 125 may be at least partially disposed in the non-conductive adhesive 155. In one exemplary implementation, the non-conductive adhesive 155 may include a hot melt adhesive. The non-conductive adhesive 155 may include a light-blocking material that prevents light generated by the light source 125 from propagating between the first and second substrates 135, 140.

FIG. 3 illustrates an exemplary representative circuit of the light sheet 110 illustrated in FIG. 2A. In the representative circuit, the top layer 160A acts as an electrical shield. The bottom layer 160B is electrically connected to the light source 125, illustrated as a light emitting diode, and the resistive element 145, illustrated as a resistor.

Figure 4:
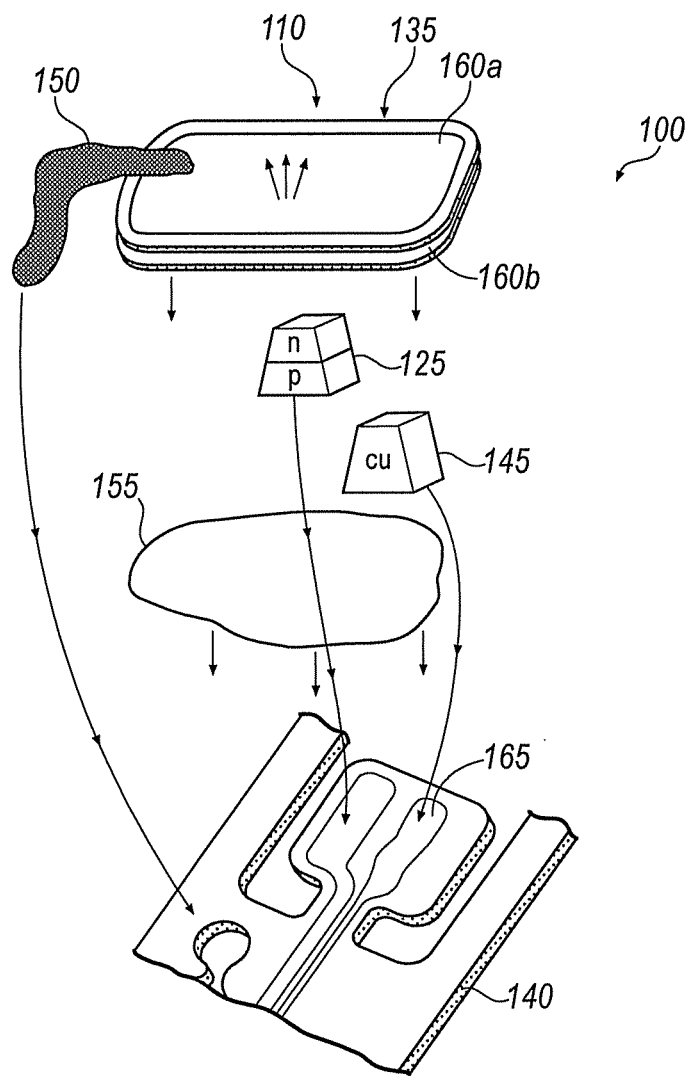
FIG. 4 illustrates an exemplary assembly view of the sensor of FIG. 2.

FIG. 4 illustrates an exemplary assembly view of the light sheet 110 illustrated in FIG. 2. The first substrate 135 and the second substrate 140 may be formed using a hot melt technique. For instance, the non-conductive adhesive 155 may be heated until it is in liquid form and placed on the second substrate 140. The light source 125 and resistive element 145 may be placed on the second substrate 140 prior to the non-conductive adhesive 155 being applied. Once applied, the first substrate 135 may be placed on top of the non-conductive adhesive 155. When the non-conductive adhesive 155 cools, it cures to adhere the first substrate 135 to the second substrate 140. The light source 125 and resistive element 145 may be aligned with the traces disposed on the second substrate 140 prior to introducing the non-conductive adhesive 155 in heated form. Additionally, the conductive adhesive 150 may be applied to the first and second substrates 135, 140. The light sheet 110 may further be disposed within the sensor pad 105 (not shown in FIG. 4).

Figure 5:
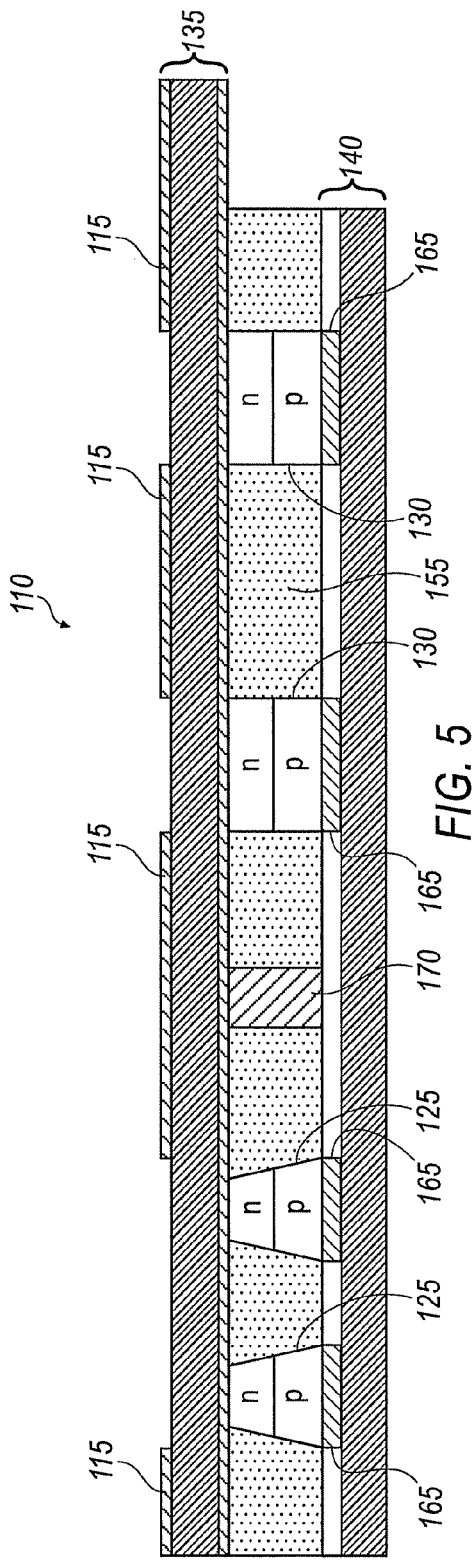
FIG. 5 illustrates an exemplary cross-sectional view of a sensor having a light active sheet material with a light source and a light detector.

FIG. 5 illustrates a cross-sectional view of an exemplary light sheet 110 having two light sources 125 and two light detectors 130. The light sheet 110 may, of course, have any number of light sources 125 and light detectors 130. The light detectors 130 illustrated are P-N junction semiconductors with an anode on the P side and a cathode on the N side. The anode of the light detector 130 is electrically connected to the traces on the second substrate 140 while the cathode of the light detector 130 is electrically connected to the bottom layer 160B of the first substrate 135. As electricity flows through the light detector 130, the light detector 130 is able to detect near-infrared light emitted by the light source 125.

The light sheet 110 of FIG. 5 further includes the light blocking pattern 115 disposed on the top layer 160A of the first substrate 135. The light blocking pattern 115 defines a plurality of openings. The openings aligned with the light sources 125 allow the light generated by the light sources 125 to propagate through, for instance, a portion of a patient's body. The openings aligned with the light detectors 130 allow the light propagated through the portion of the patient's body to be received by the light detectors 130. In one exemplary approach, the light blocking pattern 115 is integrally formed with the sensor pad 105.

The light sheet 110 of FIG. 5 further includes a light blocker 170 disposed between the first substrate 135 and the second substrate 140 to prevent light generated by the light sources 125 from propagating through the non-conductive adhesive 155 to the light detector 130. While the non-conductive adhesive 155 may have light-blocking properties, the light blocker 170 may be used to provide further protection against the light detector 130 receiving light that has not travelled through the patient's tissue.

Figure 6:
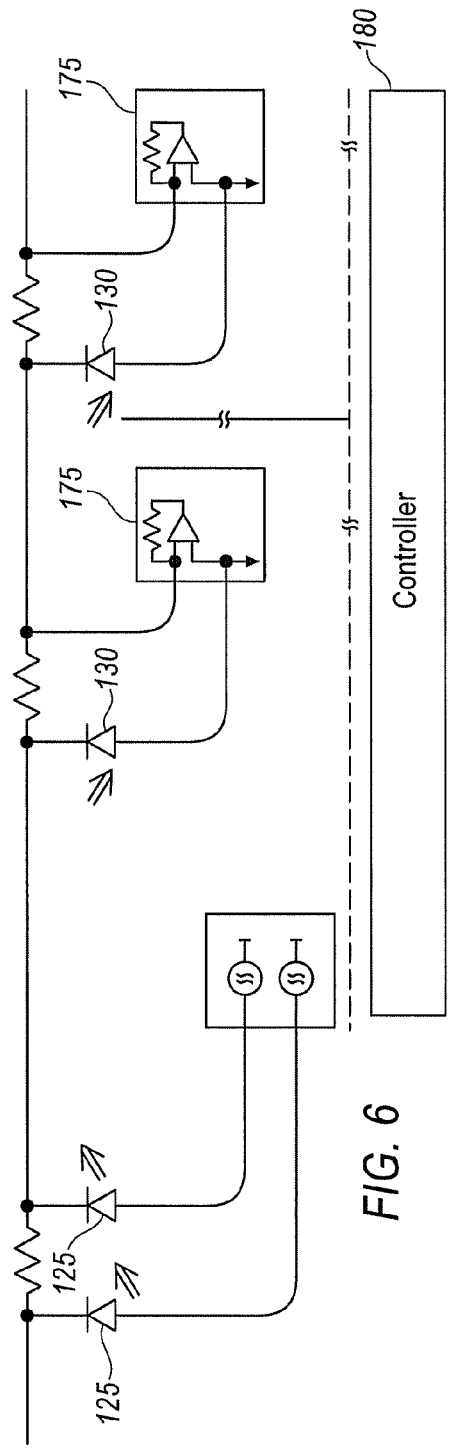
FIG. 6 illustrates an exemplary representative circuit of the sensor of FIG. 5.

FIG. 6 illustrates an exemplary representative circuit of the light sheet 110 of FIG. 5. The circuit includes the light sources 125 represented as light emitting diodes with a resistor disposed therebetween. The resistor may be used to control the current flow through the light sources 125. The light sources 125 receive control signals from a controller. The light detectors 130 are represented as photodiodes. Each photodiode outputs a signal representative of the oxygen saturation of the tissue in which the near-infrared light was propagated. The photodiodes may be connected to one or more processing circuits 175, such as an amplifier circuit, prior to transmitting the signal to the controller 180 in order to process the signal prior to, for instance, displaying the signal on a display device.

Figure 7:
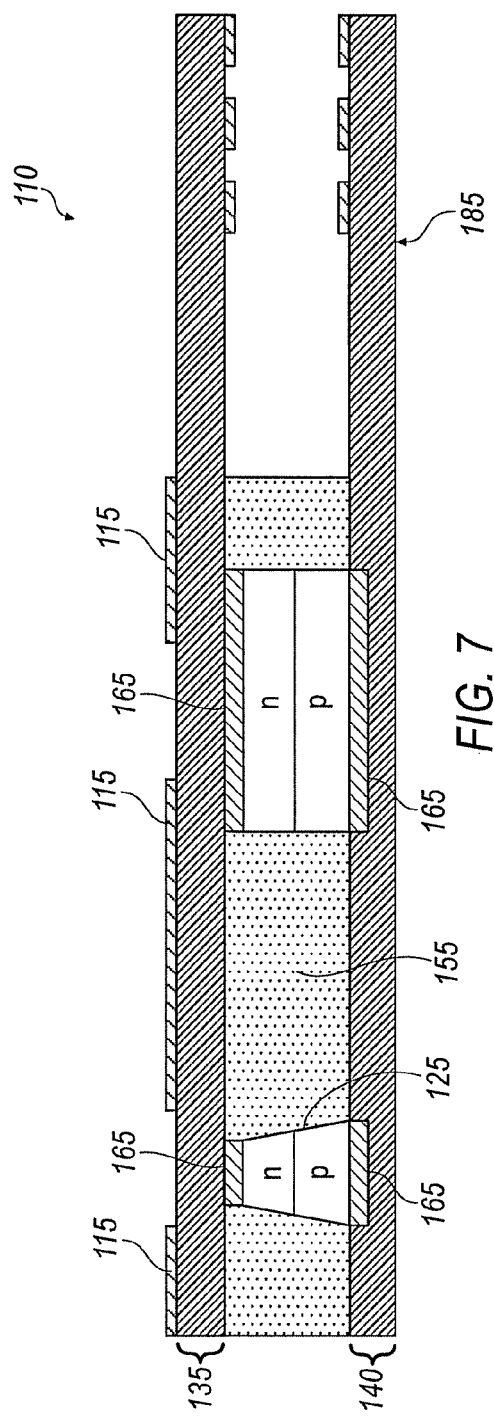
FIG. 7 illustrates an exemplary cross-sectional view of a sensor having a light active sheet material and a connector.

FIG. 7 illustrates another exemplary cross-sectional view of a light sheet 110 having an integrated connector 185. Also, in the implementation illustrated in FIG. 7, the light source 125 and light detector 130 are electrically isolated from one another. In the previous implementations, the light source 125 and light detector 130 were electrically connected via the bottom layer 160B of the first substrate 135. In this exemplary approach, the light source 125 and light detector 130 are connected to traces 165 disposed on the first substrate 135.

Figure 8:
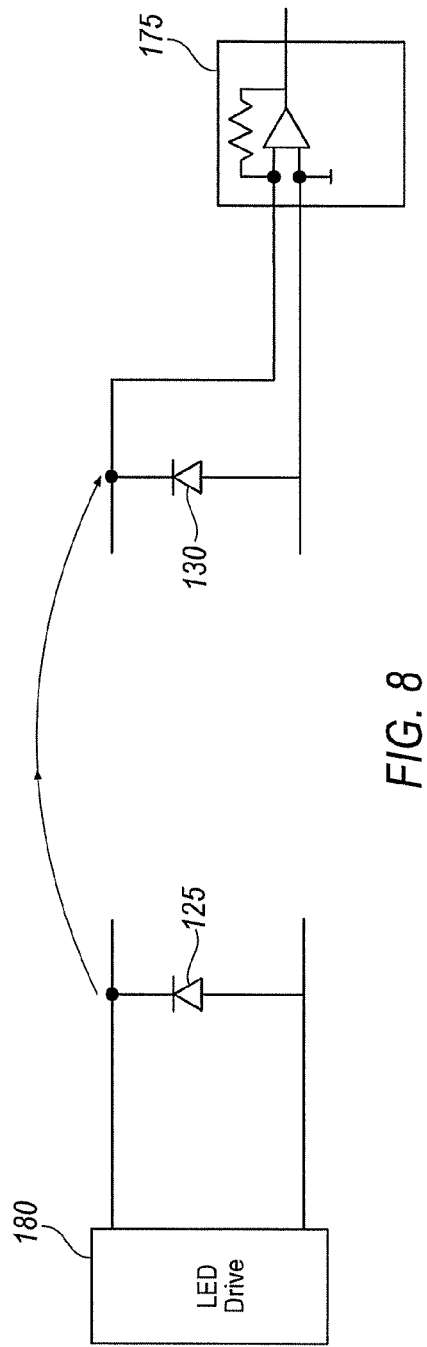
FIG. 8 illustrates an exemplary representative circuit of the sensor of FIG. 7.

FIG. 8 illustrates an exemplary representative circuit of the light sheet 110 of FIG. 7. The controller is configured to control the operation of the light source 125. Light travels through the patient's tissue and is received at the light detector 130. The light detector 130 generates a signal representative of the oxygen saturation of the tissue through which the light was propagated and that signal is transmitted from the light detector 130 to the processing circuit.

Figure 9:
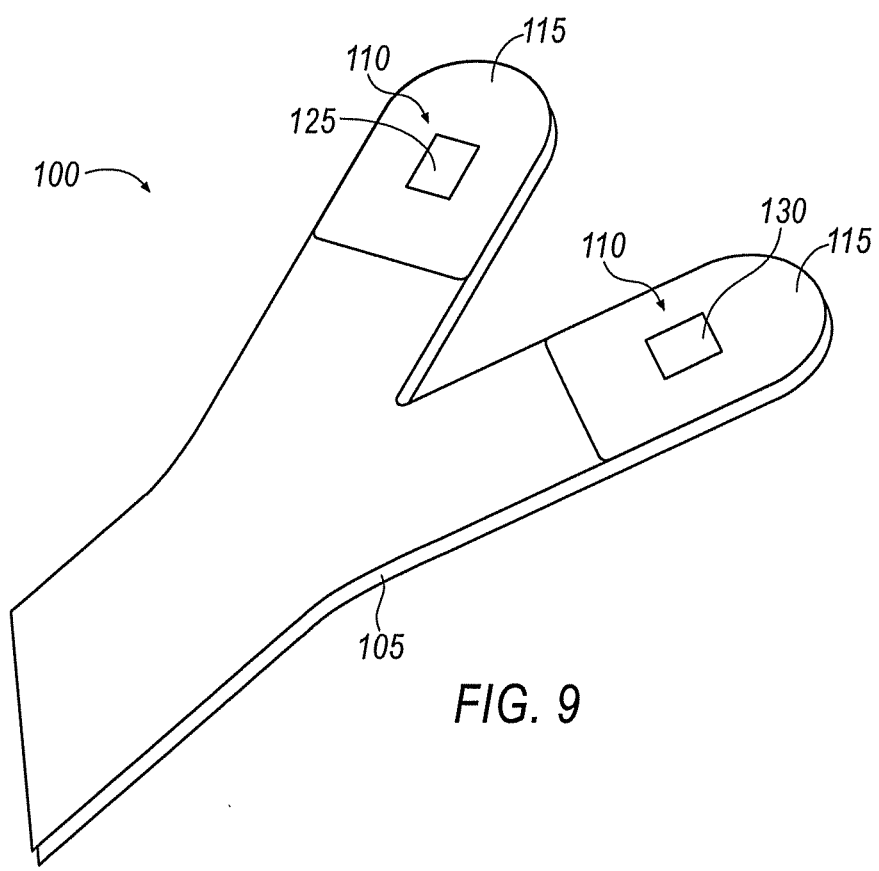
FIG. 9 illustrates an exemplary sensor with two light active sheets that are electrically isolated from one another.

FIG. 9 illustrates an exemplary sensor 100 having two light sheets 110 that are isolated from one another. One light sheet 110 includes one or more light sources 125 and the other light sheet 110 includes one or more light detectors 130. The sensor pad 105 may be placed on a portion of the patient's body. The sensor pad 105 may define openings to allow light to propagate from the light source 125 to the light detector 130. Moreover, the sensor pad 105 may include an adhesive to fix the sensor 100 in place relative to a patient's body.

In general, computing systems and/or devices, such as the controller, may employ any of a number of well known computer operating systems, including, but by no means limited to, known versions and/or varieties of the Microsoft Windows® operating system, the Unix operating system (e.g., the Solaris® operating system distributed by Sun Microsystems of Menlo Park, Calif.), the AIX UNIX operating system distributed by International Business Machines of Armonk, N.Y., and the Linux operating system. Examples of computing devices include, without limitation, a computer workstation, a server, a desktop, notebook, laptop, or handheld computer, or some other known computing system and/or device.

Computing devices generally include computer-executable instructions, where the instructions may be executable by one or more computing devices such as those listed above. Computer-executable instructions may be compiled or interpreted from computer programs created using a variety of well known programming languages and/or technologies, including, without limitation, and either alone or in combination, Java™, C, C++, Visual Basic, Java Script, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of known computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

CONCLUSION

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be apparent upon reading the above description. The scope of the invention should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the invention is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A sensor comprising:
a sensor pad configured to be disposed on a portion of a patient's body; and
a light sheet disposed on the sensor pad and having a first substrate and a second substrate at least partially spaced from one another, wherein the light sheet includes a light source and a light detector and wherein the light source and the light detector are disposed between the first and second substrates such that the light source is configured to emit near-infrared light through the first substrate into the patient's body and the light detector is configured to detect near-infrared light reflected from the patient's body through the first substrate,
wherein the first substrate includes a first layer having a conductive pattern and a second layer having a conductive pattern and wherein the first layer and the second layer are separated by a non-conductive spacer material,
wherein the light source and the light detector are both electrically connected between the second substrate and the second layer of the first substrate.

2. The sensor as set forth in claim 1, further comprising a non-conductive adhesive disposed between the substrates.

3. The sensor as set forth in claim 2, wherein the non-conductive adhesive is configured to prevent the light detector from receiving light generated by the light source through the non-conductive adhesive.

4. The sensor as set forth in claim 1, further comprising a light blocker disposed between the substrates and configured to prevent the light detector from receiving light travelling between the substrates.

5. The sensor as set forth in claim 1, wherein at least the first substrate is transparent to near-infrared light.

6. The sensor as set forth in claim 1, wherein the second substrate includes an electrically conductive pattern.

7. The sensor as set forth in claim 6, wherein the light source and the light detector are in electrical communication with one another via the electrically conductive pattern.

8. The sensor as set forth in claim 1, further comprising a light-blocking pattern disposed on at least one of the substrates.

9. The sensor as set forth in claim 8, wherein the sensor pad is non-conductive.

10. The sensor as set forth in claim 9, wherein the sensor pad is configured to prevent ambient light from interfering with the light detector.

11. A light sheet comprising:
a first substrate having a first layer having a conductive pattern and a second layer having a conductive pattern, wherein the first layer and the second layer are separated by a non-conductive spacer material;
a second substrate at least partially spaced from the first substrate;
a light source disposed between the first substrate and the second substrate and configured to emit near-infrared light through the first substrate; and
a light detector disposed between the first substrate and the second substrate and configured to detect near-infrared light through the first substrate;
wherein the light source and light detector are electrically connected between the second layer of the first substrate and the second substrate.

12. The light sheet as set forth in claim 11, further comprising a non-conductive adhesive disposed between the substrates and configured to prevent the light detector from receiving light generated by the light source through the non-conductive adhesive.

13. The light sheet as set forth in claim 11, further comprising a light blocker disposed between the substrates and configured to prevent the light detector from receiving light travelling between the substrates.

14. A sensor comprising:
a sensor pad configured to be disposed on a portion of a patient's body;
a first light sheet having a light source configured to emit near-infrared light; and
a second light sheet electrically isolated from the first light sheet and having a light detector configured to detect near-infrared light,
wherein the first light sheet and the second light sheet each include first and second substrates,
wherein the first substrates of the first and second light sheets both include a first layer having a conductive pattern and a second layer having a conductive pattern and wherein the first layer and the second layer are separated by a non-conductive spacer material,
wherein the light source is electrically connected between the second layer of the first substrate and the second substrate,
wherein the light source is configured to emit near-infrared light through the first substrate and the light detector is configured to detect near-infrared light through the first substrate.

15. The sensor as set forth in claim 14, wherein the first light sheet and the second light sheet each include a non-conductive adhesive disposed between the substrates.

* * * * *